United States Patent
Ferreira De Sa et al.

(10) Patent No.: US 9,623,226 B2
(45) Date of Patent: Apr. 18, 2017

(54) DEVICE FOR EFFICIENT DELIVERY OF COMPOUNDS TO OR THROUGH THE SKIN OR BIOLOGICAL BARRIERS, USING LIGHT-ABSORBING THIN FILMS

(75) Inventors: Goncalo Fernando Ferreira De Sa, Coimbra (PT); Carlos Alberto Lourenco De Serpa Soares, Coimbra (PT); Luis Guilherme Da Silva Arnaut Moreira, Coimbra (PT)

(73) Assignee: Universidade de Coimbra, Coimbra (PT)

( * ) Notice: Subject to any disclaimer, the term of this patent is extended or adjusted under 35 U.S.C. 154(b) by 824 days.

(21) Appl. No.: 14/113,148

(22) PCT Filed: Apr. 19, 2012

(86) PCT No.: PCT/PT2012/000013
§ 371 (c)(1),
(2), (4) Date: Oct. 21, 2013

(87) PCT Pub. No.: WO2012/144916
PCT Pub. Date: Oct. 26, 2012

(65) Prior Publication Data
US 2014/0046246 A1    Feb. 13, 2014

(30) Foreign Application Priority Data

Apr. 19, 2011   (PT) .......................................... 105635

(51) Int. Cl.
*A61M 37/00*   (2006.01)
*A61K 41/00*   (2006.01)
*G10K 15/04*   (2006.01)
*A61N 5/06*    (2006.01)
*C12N 15/87*   (2006.01)

(52) U.S. Cl.
CPC ..... *A61M 37/0092* (2013.01); *A61K 41/0047* (2013.01); *A61M 37/00* (2013.01); *A61N 5/06* (2013.01); *C12N 15/87* (2013.01); *G10K 15/046* (2013.01)

(58) Field of Classification Search
CPC ...... A61K 41/0047; C12N 15/87; A61N 5/06; A61M 37/00; A61M 37/0092; G10K 15/046
See application file for complete search history.

(56) References Cited

U.S. PATENT DOCUMENTS

| | | | |
|---|---|---|---|
| 2001/0055435 A1 | 12/2001 | Biagi et al. | |
| 2013/0190595 A1* | 7/2013 | Oraevsky | A61B 5/0095 600/407 |
| 2014/0046246 A1* | 2/2014 | Ferreira De Sa | A61K 41/0047 604/22 |

FOREIGN PATENT DOCUMENTS

WO    97/07734 A1    3/1997

OTHER PUBLICATIONS

International Search Report for PCT/PT2012/000013 dated Oct. 15, 2012.

\* cited by examiner

*Primary Examiner* — Daniel Pihulic
(74) *Attorney, Agent, or Firm* — Sughrue Mion, PLLC

(57) ABSTRACT

This invention refers to a device capable of rapidly and efficiently converting the energy in a laser pulse into a high-impulse broadband pressure wave and to its applications in the transient permeabilization of a biological membrane, including the outer layers of the skin, without causing damage or discomfort. A method to deliver drugs and biologically active compounds to or through the skin, or biological barriers, with this device is also disclosed.

20 Claims, 11 Drawing Sheets

A　　　　　　　　　B

DEVICE FOR EFFICIENT DELIVERY OF COMPOUNDS TO OR THROUGH THE SKIN OR BIOLOGICAL BARRIERS, USING LIGHT-ABSORBING THIN FILMS

BACKGROUND OF THE INVENTION

This invention refers to a device capable of rapidly and efficiently converting the energy in a laser pulse into a high-impulse pressure wave and to its applications in the transient permeabilization of a biological barrier, including the outer layers of the skin, without causing damage or discomfort. The invention is described in terms of the physical principles of efficient laser generation of pressure waves, of the properties of the absorbing materials that maximize the amplitude of the pressure wave and minimize its rise time, and of the practical delivery of drugs or biologically active compounds to or through the skin or other biological barriers. Examples are given to illustrate the use of the device and its applications. The distinctive features of the device are the use of thin films (thickness <200 µm) strongly absorbing the light of pulsed lasers and the use of affordable pulsed lasers, such as lasers with low energies (laser energy <500 mJ), wherein the said device is capable of generating high impulse acoustic transients with short rise times (rise time <50 ns) at low optical power densities (<40 $MW/cm^2$ per pulse).

The skin is a very effective protection against the ingress of foreign material, such as chemicals and microbes. The outermost layer of the skin, called stratum corneum (SC), is only 10 to 20 µm thick but it is the main contributor to the skin's impermeability. It is made by a dozen layers of hardly packed nonliving corneocyte cells, embedded in a mixture of lipids with high spatial organization. Most molecules penetrate the skin by diffusion through the intercellular lipids, a tortuous path around the corneocytes that is highly constrained by structural and solubility requirements. Underneath the SC there is the viable epidermis, which is 50 to 100 µm thick and is vascular. Further below is the dermis, 1-2 mm thick and rich in capillaries, capable of clearing most penetrants within minutes [1].

The idea of delivering drugs through the skin is centuries old. The attempts to attain this goal can be classified in two groups: passive and active drug delivery [2]. The first class refers to formulations of vehicles optimized to enhance the diffusion of a particular drug through the skin, including ointments, creams or gels, which may include chemical permeation enhancers. Indeed, a wide variety of chemicals have the ability to increase skin permeability, such as dimethyl sulfoxide, laurocapram (Azone), 2-n-nonyl-1,3-dioxolane (SEPA), fatty acids and fatty acid esters, surfactants, and others well known in the art [3]. However, the increased permeation enhancement, even of small molecules, typically correlates with increased skin irritation [4]. Passive methods are only efficient for transdermal delivery of small molecules (molecular weight <500 Da) with adequate lipophilicity (n-octanol-water partition coefficients $K_{OW}$, in the range $1<(\log K_{OW})<3$) and with less than 3 hydrogen-bonding groups. Moreover, the formulation of the vehicle is specific for a given drug. Active drug delivery methods employ physical methods such as electrical assistance (iontophoresis, electroporation), mechanical processes (microneedles, abrasion, ablation, perforation, microprojections), or ultrasounds (sonophoresis). Another active method of drug delivery consists in generating photomechanical waves by intense pulsed-laser irradiation of a target [5]. The stress waves formed by optical breakdown, ablation or thermoelastic expansion have been shown to transiently permeabilize the SC and facilitate the transport of macromolecules into the viable epidermis [6].

Technical applications of stress waves in the delivery of compounds through epithelial cell layer have been described. For example, Kollias et al [7] described in U.S. Pat. No. 6,251,099 B1 a compound delivery using impulse transients generated by lasers with fluences between 1 and 7 $J/cm^2$ and pulse widths of 20-30 ns, which correspond to optical power densities between 40 and 300 $MW/cm^2$. These intense and short laser pulses were directed to targets with thickness ranging from 0.8 mm (for metals) to 3 mm (for plastics). At these optical power densities, the dominant mechanism of interaction between the laser pulse and the target is ablation of the target material and is usually accompanied by plasma formation. This produces ejection of material from the surface of the target hit by the laser pulse and the associated recoil momentum propagates in the bulk of the target to reach its opposite surface as an acoustic wave. The ability of this acoustic wave to increase temporarily the permeability of the skin has been related to its impulse. Intradermal delivery of large compounds without damaging the skin requires impulses between 2 and 50 bar/ns [5]. The generation of pressure waves with such high impulses in a useful area of a current target requires lasers with high power densities that are recognized as complex and costly, and alternatives have been sought [8].

Apparatus for enhancing drug delivery using optical power densities down to 10 $mJ/cm^2$ were also described. For example, Visuri et al [9] described in U.S. Pat. No. 6,484,052 B1 how such low power densities at laser pulse frequencies between 100 Hz and 1 MHz can be coupled to a fiber optic and inserted in a portion of a human body to generate an acoustic radiation field in that portion. They also described the attachment of an optically-powered mechanical transducer to the distal end of said fiber, but failed to specify the characteristics of such a transducer. Unless the transducer has very specific physical, photochemical and material properties, it will not be able to produce a pressure wave capable of transiently permeabilizing biological barriers. The use of high laser pulse frequencies, rather than a single or a small number of laser pulses, does not change the properties of the pressure waves. Hence, no optically-powered mechanical transducer capable of producing acoustic waves capable of permeabilizing biological barriers was disclosed.

In another field, that of biological tissue spectral characterization, Biagi et al described in U.S. Pat. No. 6,519,376 B2 an opto-acoustic generator to generate acoustic, or ultrasound, waves from a pulsed laser-energy source [10]. The absorption of a laser pulse by a graphite-containing layer applied to the tip of an optical fiber connected to the laser source was shown to efficiently produce very-wide-band acoustic pulses. Pure graphite films can also be produced with sub-micrometer thicknesses and still have sufficient mechanical resistance to be handled in pieces of 2.5 cm in diameter [11]. Moreover, with a thickness of 50 nm, the apparent absorptance of these films approaches unity at 400 nm. Free-standing graphite films with very short-lived excited states [12] can be conveniently prepared by pyrolysis of polyacrylonitrile. However, acoustic pulses generated by this method with graphite-containing layers were never considered for drug delivery because the field of tissue characterization employs microjoule laser pulses [13] and this is insufficient for drug delivery with therapeutic effects. Actually, therapeutic effects are not desirable in the spectral characterization, or diagnostic, of biological tissues.

The plethora of transdermal delivery systems does not obscure the fact that they remain a minor alternative to oral delivery or hypodermic injections. A simple and economic transdermal delivery method, capable of delivering a wide variety of drugs through the skin without causing pain or discomfort, and that allows the skin to recover its protective function a few minutes after the application, would confer to transdermal delivery the same status in medical practice as oral delivery or hypodermic injections.

DESCRIPTION OF THE INVENTION

This invention discloses a device to deliver molecules, macromolecules or even larger biological materials through biological barriers, including the skin or soft tissues or cell membranes, that meets the ideal characteristics mentioned above for biological delivery. The method to deliver drugs and biologically active compounds with this device is based on the fast and efficient production of a broadband, high-frequency and high-impulse acoustic transient upon short pulsed laser light absorption by a thin film, and its efficient acoustic coupling to the biological barrier, including the skin or mucosa. In the following, we employ "thin film" to describe a layer of material with a thickness smaller than 200 µm and larger than a molecular layer (typically larger than 1 nm), deposited on a thicker and more rigid (high acoustic impedance) material. It is a central object of the present invention to describe the molecular properties of the thin film that contribute to the fast and efficient generation of a pressure wave, including the requirement that this film contains chromophores that absorb most of the incident laser light and the requirement that these chromophores release the energy absorbed by radiationless processes with a lifetime comparable or shorter than the laser pulse width. The efficiency of the method is demonstrated with the delivery of large molecules and proteins to the skin and gene transfection to living cells with optical power densities of 10 MW/cm$^2$ per pulse, or less.

A. Definitions

For the purpose of this application, the following definitions will apply:
"Laser fluence" is the laser energy per unit area on the work material, expressed in units of J/cm$^2$.
"Laser pulse duration" $\tau_L$ is the full width at 1/e level of the laser pulse [14], and is conveniently expressed in units of nanosecond, ns.
"Optical power density" is the power density of a laser beam, where the power density is the power of the laser by unit irradiation area, expressed in W/cm$^2$ or more conveniently in MW/cm$^2$.
"Ablation" is the removal of material because of the incident light. In polymers this removal can be by photochemical changes that include a chemical dissolution of the polymer.
"Acoustic transient" is employed to describe both hypersonic shock waves and sonic acoustic waves [15].
"Impulse of an acoustic transient" is defined as the rate of pressure increase per unit of time, expressed in units of bar/s or more conveniently in bar/ns.
"Rise time of an acoustic transient" is defined as the time from 10% to 90% of the peak pressure [5].
"Broadband" is a wide frequency band that covers a continuous frequency spectrum and when used to qualify a pressure wave designates an acoustic emission with significant frequency components of tens of MHz.
"Photoacoustic reference compound" is a compound that absorbs the radiative energy of a laser pulse and rapidly transforms that energy into heat by radiationless processes, while returning to its ground electronic and/or vibrational state. As it is known in the art, a PAC reference compound produces the photoacoustic wave of the highest possible intensity by the absorption of a laser pulse of a given energy and in a given configuration in the absence of net chemical reactions, within the duration of the laser pulse [16, 17].
"Optical penetration depth" $\delta$ is the depth at which the intensity of the radiation inside the material falls to 3/e, conveniently expressed in cm.
"Linear decadic absorption coefficient" $\mu_a$, or linear absorption coefficient, is the absorbance divided by the optical path length through the sample, and is expressed in cm$^{-1}$.

B. Physical Principles

There are various methods described in the literature whereby a pressure wave is produced as the result of the interaction of a short laser pulse with a given material [18]. The three most important interaction mechanisms are dielectric breakdown, vaporization or material ablation, and thermoelastic processes. High laser fluences are required to produce optical breakdown with consequent formation of plasma and subsequent production of an intense shock wave. Intermediate laser fluences interact with absorbing liquids or with transparent liquids near an absorbing solid boundary to produce rapid thermal expansion and explosive vaporization or, for some materials, ablation. Lower laser fluences impinging on absorbing materials produce thermoelastic expansion of the materials. Plasma formation due to dielectric breakdown leads to high-pressure waves, but the high energies required and its destructive nature, are not practical for transient skin permeabilization. The pressure wave generated by explosive vaporization or material ablation may have the form of a shock wave, as with the plasma formation, as the ejection of material from the surface hit by the laser pulse produces a recoil momentum. The shock wave propagates in the bulk of the material and reaches the opposite surface as an acoustic wave, because the shock wave dissipates rapidly and continuous as an acoustic wave which then decays more slowly with the propagation length [19]. The spatial extent of the shock waves is limited to tenths of millimeters [15, 19]. On the other hand, transient thermoelastic expansion generates an acoustic wave. The acoustic waves resulting from ablation or thermoelastic expansion have been named "impulse transients" and employed in the transient permeabilization of epithelial cell layers [7].

The generation of photoacoustic waves by thermoelastic expansion of a confined absorbing medium can be achieved at low laser fluences (below the ablation threshold that depends on the material but is typically above 50 mJ/cm$^2$), may occur within the duration of the laser pulse ($\tau_L$) and is non-destructive. Thermoelastic expansion is believed to be an inefficient method to produce a pressure wave from a laser pulse [20, 21], and the usual sub-0.1% efficiency of the thermoelastic expansion mechanism is assumed uncompetitive with the 30% efficiency that can be attained by ablation and plasma formation mechanisms [22]. This current belief motivated the use of laser fluences above the ablation threshold to generate impulse transients capable of transiently permeabilizing the stratum corneum.

However, the maximum pressure amplitude $p_{max}$ that can be generated by thermoelastic expansion following the absorption of a laser pulse by a material confined by a rigid boundary is [18]

$$p_{max} = \frac{c_s \alpha}{C_p} I_0 \quad (1)$$

where $\alpha$ is the coefficient of thermal expansion, $C_p$ the specific heat capacity at constant pressure, $c_a$ the speed of sound of the medium and $I_0$ the peak optical power density. For example, a confined polystyrene target ($c_s$=2320 m/s, $c_p$=2 J/(g K) and $\alpha$=7×10$^{-5}$ K$^{-1}$) absorbing a 5 ns laser pulse with 50 mJ in 1 cm$^2$ ($I_0$=10 MW/cm$^2$) should be able to produce a maximum pressure of 80 bar. This is an order of magnitude less than the typical peak pressure for transdermal drug delivery with a pressure wave [5], but if the rise time of the photoacoustic wave accompanies the laser pulse width ($\tau_L$=5 ns), its maximum impulse will reach 15 bar/ns. Such an impulse is more than sufficient to permeabilize the stratum corneum. Thus, the efficient conversion of the laser pulse energy into a thermoelastic expansion making use of fast radiationless transitions from the initially populated excited state to the ground state of the chromophore rigidly confined in a narrow region, as in the photoacoustic calorimetry (PAC) technique [17, 23], should be able to produce an acoustic wave with an impulse capable of permeabilizing the stratum corneum.

The amplitude of a photoacoustic wave produced in an optically thin front-face PAC cell is given by [23]

$$\Delta P = \frac{1}{Ah} \frac{\alpha}{C_P \rho \beta} H_{th} \quad (2)$$

where A is the irradiated area, h the PAC cell thickness and $H_{th}$ the amount of thermal energy released. □, the isothermal compressibility ($\beta$), $C_p$ and the density ($\rho$) refer to the absorbing medium inside the cell. The thermoelastic properties of a solid absorbing medium are conveniently characterized by the dimensionless Grüneisen coefficient $$\Gamma = \frac{\alpha}{C_P \rho \beta} = \frac{\alpha c_s^2}{C_P} \quad (3)$$

where $C_p$ is the specific heat capacity of the sample. The physics for optically thin samples also apply to cases where the absorptance of the sample is approx. 1, if the bottom interface in totally reflecting and the light traverses twice the absorbing medium [24]. The dependence between the amplitude of the photoacoustic wave and the thickness of the light absorbing material was also observed when heavily absorbing films are employed as targets of the laser pulse [13]. The maximum pressure produced by the thermoelastic process was found to increase as the thickness of the absorbing film is reduced and this property was used in the design more efficient photoacoustic generators of ultrasound waves [10].

The importance of the thickness of the absorbing material has been overlooked in previous applications of laser pulses to produce impulse transients that permeabilize the skin. Orienting the choice of the materials by their opacity and rigidity, which are necessary but not sufficient conditions for optimal device operation, leads to an imprecise choice of metal targets thicker than 0.8 mm or of plastic targets thicker than 1 mm as absorbing materials [7]. FIG. 1 compares the acoustic transients produced when the same laser pulse intensity is absorbed by a 1 cm$^2$ surface of a 1 mm thick black plastic or by a 10-30 micrometer thick films with strong absorption at the excitation wavelength, both confined by a glass cover and absorbing more than 80% of the laser light. With the decrease of target thickness, the amplitude of the pressure waves increases as shown in FIG. 2. This fact changes the paradigm of high-pressure transient impulse generation by pulsed lasers, because it becomes possible to reduce dramatically the energy of the pulsed laser source by optimizing the device that converts the laser pulse energy in a photoacoustic wave.

Maximizing the efficiency of the laser energy conversion into an acoustic transient via thermoelastic processes requires the choice of materials that convert the laser pulse energy into heat with the duration of the laser pulse, thin films (low h) with absorptances higher than unit, and materials with large Grüneisen coefficients. Therefore, a device aimed at the fast and efficient conversion of the energy of a laser pulse into a photoacoustic wave must incorporate in a very thin layer a compound that strongly absorbs light at the wavelength of the laser pulse and that converts into heat all the energy absorbed during that laser pulse. PAC reference compounds meet these properties. The intensity of the photoacoustic wave may be further increased if ultrafast structural volume changes accompany the radiationless decay occurring within the duration of the laser pulse.

It has not been appreciated in earlier applications of high-pressure impulse transients to transdermal delivery of compounds that the properties of the absorbing materials are decisive in determining the shape and amplitude of the transient pressure. FIG. 3 shows simulations for one transient with various decay times and for two transients with different decay times and fractions of laser energy released. When measured by a 2.25 MHz transducer, the amplitude of acoustic transients decrease by a factor of 2 when the lifetime of the transient electronic state increases from 10 to 100 ns, even when all the laser energy is converted into heat. The rise time of the acoustic transient is also displaced towards longer times, as expected. When two transients are present and one of them has a lifetime longer than the laser pulse, the outcome is always a smaller acoustic transient than that can be obtained with a PAC reference compound, unless the products have a larger volume than the reactants or the standard enthalpy of the products is less than that of the reactants and the reaction is exothermic.

Exothermic reactions may produce more heat, and hence more intense acoustic transients, than PAC reference compounds. The amplitude of such acoustic transients is further increased if the exothermic reactions are accompanied by an increase in structural volume due to the fragmentation of the materials, as is usually the case of laser-induced ablation. However, the impulse of these acoustic transients will only be increased if the rise time of the acoustic transient remains short. Stress transients generated by thermoelastic expansion at sub-ablation laser fluences follow $\tau_L$ when PAC reference materials are employed as chromophores because by definition their lifetimes are shorter than $\tau_L$, and have a bipolar signature with compressive and tensile components. It is known that when the laser fluence exceeds the ablation limit, an additional compressive wave is observed at latter times due to the ablative recoil [25]. The rise time of the ablative recoil decreases as the laser fluence increases and does not depend on $\tau_L$ [25, 26]. The mechanism of pressure production by laser ablation involves bubble growth, which has a growth time of approx. 100 ns and places a lower limit for pressure pulse widths [20]. For laser fluences much higher than the ablation threshold, the high intensities of acoustic transients compensate for their relatively long rise times, and large impulse transients can be created. Although this is well known in the art [5], it does not meet the need for a simple and affordable laser source for active transdermal delivery of a wide variety of compounds, or plasmid transfection through cell membranes. Thin films of materials with low nanosecond pulsed laser ablation thresholds, preferably less than 50 mJ/cm, may overcome these limitations. Pulsed laser ablation thresholds below 50 mJ/cm$^2$ have been reported for some polymer films with high linear absorption coefficients at the excitation wavelength [27, 28].

Very high linear absorption coefficients are also important because the spectral band of the photoacoustic transient is determined by the spectral band of the laser pulse when [14]

$$\mu_a c_s \tau_L \square l \qquad (4)$$

where $\tau_L$ the laser pulse duration. Thus, the acoustic transient profile will follow that of a $\tau_L=10$ ns laser pulse in a typical polymer ($c_s=2500$ m/s) when $\mu_a>>400$ cm$^{-1}$. When sufficient quantities of PAC reference compounds are incorporated in appropriate supporting materials such that the optical penetration depth ($\delta=1/(2.3\mu_a)$) is smaller than 10 μm, the duration of the nanosecond laser pulse and its peak power determine the bandwidth and intensity of the acoustic transient. The amplitude of the acoustic transients decreases when $\tau_L$ is significantly larger than the ratio of optical penetration depth to the velocity of the longitudinal waves, and the decrease of the acoustic transient amplitude with the increase in $\tau_L$ is more accentuated at high frequencies [29]. The fast and efficiently conversion of the laser pulse energy generates very wide band acoustic transients, with bandwidths in the tens or hundreds of MHz, depending on the laser pulse width. For sufficiently short laser pulses, the center frequency of the generated ultrasound is displaced to higher frequencies when the optical penetration depth of the absorbing material is decreased. For example, for Nd:YAG laser excitation at 1064 nm, graphite-based materials have optical penetration depths of 10 to 50 microns, whereas the optical penetration depth of aluminum is 10 nm, and this displaces the center frequency of the generated ultrasound from 2.1 to 12 MHz [30]. The fast Fourier transforms of acoustic transients reveal this property, as shown in FIG. 4. This experiment employed a 225 MHz transducer because the high-frequency components of the bandwidth are best measured with high-frequency transducers.

It is desirable for the transient permeabilization of the skin and mucosa that the bandwidth of the acoustic transient extends to high frequencies (frequencies higher than 20 MHz) because threshold of cavitation is displaced towards higher energies at higher frequencies, although high frequencies are more strongly absorbed by biological tissues. Transient cavitation bubbles should be avoided because they can cause damage in biological tissues as they expand to millimeter sizes and then collapse. The likelihood that exposure to acoustic transients produces inertial (or transient) cavitation is measured by the mechanical index (MI)

$$MI = \frac{p_{rmax}}{\sqrt{f}} \qquad (5)$$

where $p_{rmax}$ is the peak rarefactional (tensile) pressure and f is the centre (nominal) frequency of the acoustic transients.

A higher value of MI indicates a higher probability of cavitation and therefore the equation above means that the minimum pressure amplitude that satisfies the cavitation threshold increases with the ultrasonic frequency [31, 32]. On the other hand, the attenuation of a 10 MHz acoustic frequency by a 3 cm water path is only 7%, but it increases to 85% for a 50 MHz pressure component [20]. Very high frequencies are present in acoustic transients when short laser pulses ($\tau_L<20$ ns) are absorbed by PAC references confined in very thin layers (less than 10 microns thick). The PAC references must have a very high absorption coefficient at the laser pulse wavelength to absorb most of the laser pulse within the thickness of the film where they are incorporated. In view of the acoustic attenuation referred above, it is also desirable that the source of the PAC wave is close to the skin.

The design of devices with very small absorption layers confined in thin supports must also consider the limits for what can be considered the generation of a planar acoustic wave. The criterion is that the laser beam radius r must be chosen to meet the condition $$r>>\sqrt{2c_s\tau_L z} \qquad (6)$$

where $c_s$ is the speed of sound in the sample, $\tau_L$ is the laser pulse width and z is the distance between the absorbing layer surface and the detector. A structural support with z=11 mm, with values of $c_s=2500$ m/s and $\tau_L=10$ ns, requires r>>0.2 mm. Hence, it is possible to focus a laser beam to a radius of 1 mm and still produce a planar acoustic wave. The remarkable advantage of a device with this configuration is that an energy density of 10 mJ/cm$^2$ per pulse on an area of 0.03 cm$^2$ corresponds to a laser pulse of 0.3 mJ. Energies of this magnitude for pulse durations of a few nanoseconds are readily available in pulsed fiber lasers, diode-pumped crystal lasers and other solid-state lasers, which also attain frequencies of hundreds of kHz. Such lasers are portable, compact, durable, affordable, easy to operate and do not require maintenance.

The design of efficient photoacoustic converters of laser pulse energy must also consider that the generation of the pressure wave in the presence of a rigid boundary leads to a higher pressure than in the case of a free boundary [18]. The acoustic constrain of the photoacoustic converter by quartz plates was shown to enhance the amplitude of 20-MHz photoacoustic waves by a factor of nearly 100 [33]. Moreover, in the case of an acoustic transient generated by thermoelastic expansion, the presence of a rigid boundary transforms a stress transient consisting of a compression followed by a rarefaction into a unidirectional compressive impulse [34]. The efficient conversion of the laser pulse energy makes it possible to use laser fluences below 100 mJ/cm$^2$ to generate intense and mostly-compressive acoustic transients.

The optimization of the thermoelastic properties of the supporting material also contributes to increase the amplitude of acoustic transients generated by thermoelastic expansion of a confined thin film incorporating a PAC reference material. Organic liquids possess thermoelastic properties that can also be described by high Grüneisen coefficients, and form excellent acoustic bonds with solid surfaces [35]. Confining the thin film between a window and a thin layer of an organic liquid with high Γ further contributes to increase the efficiency of conversion of the laser pulse energy into a photoacoustic wave. Liquids as diverse as carbon tetrachloride, bromobenzene, acetone or acetonitrile have thermoelastic properties that lead to high amplitude photoacoustic waves [23]. Elastomers such as rubber, neoprene, viton or polyurethane are known to have large thermal expansion coefficients but this is sometimes compensated by other properties.

It is well known in the art that when an acoustic wave traveling in one medium (medium 1) encounters a boundary of a second medium (medium 2), reflected and transmitted (or refracted) waves are generated. The transmission coefficient is given by $$T = \frac{A_2}{A_1} = \frac{2\sqrt{Z_1 Z_2}}{Z_1 + Z_2} \quad (7)$$

where $A_2$ and $A_1$ are the initial amplitude in medium 1 and the final amplitude in medium 2, and $Z_1$ and $Z_2$ are the acoustic impedances in the two media. Complete transmission between the two media requires $Z_1=Z_2$. The presence of voids in the device is a major cause of inefficiency. Voids are frequently filled by air and its acoustic impedance is dramatically different from that of the other materials composing the device. This translates in very poor acoustic transmission and loss of efficiency of the device. Thus, it is necessary to insure a good acoustic coupling between the thin film of the device where the photoacoustic wave is generated and all the parts to the device that the photoacoustic wave must cross to reach the skin. Additionally, it is also necessary to have a good acoustic coupling between the device and the skin or the mucosa. The acoustic impedance of the skin is $Z_{skin}$=1.54 MRayl [(1 MRayl=1× $10^6$ kg/(m² s)], similar to that of water ($Z_{water}$=1.48 MRayl), but very different from that of metals ($Z_{Aluminum}$=17 MRayl, $Z_{steel}$=46 MRayl), although relatively close to those of plastics ($Z_{Teflon}$=2.97 MRayl, $Z_{polyethylene}$=1.76 MRayl, $Z_{polystyrene}$=2.42 MRayl). Interesting materials for good acoustic coupling with the skin are paraffin ($Z_{paraffin}$=1.8 MRayl), glycerol ($Z_{glycerol}$=2.3 MRayl), graphite ($Z_{graphite}$=2.7 MRayl), cellulose acetate ($Z_{cellulose}$=3.2 MRayl) or acoustic scanning gel. Efficient delivery of acoustic waves to the skin requires the choice of materials with acoustic impedances close to $Z_{skin}$. The problem of acoustic impedance mismatch may also be solved by using multiple matching layers in series where the optimum impedance for each layer is equal to the geometric mean of the impedance of the layers on either side.

C. Materials Chemistry

Strongly absorbing and rigid targets are widely available. However, the considerations detailed above also call for materials with the properties of PAC reference compounds, with high linear absorption coefficients, incorporated in a thin absorbing layer with high Grüneisen coefficients, good acoustic coupling between the light absorbing layer and all the materials where the acoustic transient propagates in the direction of the skin, with good acoustic coupling with the skin and, preferably, with reflection of the transmitted light in the back of the device to provide a second passage through the absorbing layer. Alternatively, rather than using thin films incorporating materials with the properties of PAC reference compounds, the thin light-absorbing absorbing film can be fabricated with polymers with low nanosecond pulsed laser ablation thresholds. These are the guidelines to make devices that efficiently convert laser pulse energy into high intensity, short duration and broadband acoustic transients. FIG. 5 shows a working diagram of a preferred embodiment of a device following these guidelines. The examples provided here intend to illustrate different methods to obtain materials adequate for fast and efficient conversion of laser pulse energy into an acoustic transient, but the choice of materials is only limited by the above-mentioned guidelines.

Some non-limiting examples of PAC reference compounds that can be incorporated in thin layers are ortho-hydroxybenzophenone and similar molecules undergoing ultrafast photoinduced intramolecular proton or hydrogen-atom transfers that return rapidly to the original ground state, $Mn^{III}$ complexes of meso-tetraphenylporphyrin (MnTPP) and other paramagnetic complexes with ultrafast metal-to-ligand and/or ligand-to-metal charge-transfer relaxation processes, complexes with charge-transfer bands that return to the ground state by ultrafast charge recombination, β-carotene and other systems that rapidly decay to the ground stare through conical intersections, graphite and other materials capable of ultrafast transfer of their electronic energy to phonon nodes followed by cooling in the subnanosecond time scale [36], semiconductor materials with short-lived transient states, or other materials, or mixtures of materials, with ultrafast radiationless relaxation processes. Such ultrafast radiationless processes may include, in addition to thermal relaxation, structural volume changes that rapidly result in intermediates with larger molar volumes than the reactants. The PAC reference compounds in the thin layer may also be vibrationally excited with infrared laser pulses, provided that the vibrational modes, or combination of vibrational modes, excited with infrared light return very rapidly to the ground vibrational state, as seen, for example, in the photoacoustic spectra of water and other materials.

Thin polymer films can be produced inexpensively by a number of techniques. For example, standard spin-coating produces films with thicknesses between 1 and 10 micrometers. Dyes that qualify as PAC references must be incorporated in large quantities within the polymer and the device must be designed to provide the confinement and rigidity required for efficient operation. Incorporation of larger quantities of the dye in the polymer is facilitated by the introduction of long alkyl chains, such as in meso-tetraundecyl-porphyrins. The properties of PAC references are also present in such compounds when complexed with paramagnetic ions such as $Mn^{III}$ in the presence counterions such as halide ions, carboxylates, etc. Such PAC references are identified in this work as MnTAP and presume the presence of a counterion. To illustrate the use and performance of thin polymeric films, we provide in Example 1 the method to produce a device for transdermal drug delivery with a thin polymer film incorporating large amounts of MnTAP. Another class of compounds with properties adequate to incorporate in this polymer films is that of near-infrared absorbing dyes designed, for example, for blocking near-infrared laser light. Example 2 describes the fabrication of a device with one of such dyes, which has the advantage of using near-infrared laser pulses to produce photoacoustic waves. Near-infrared lasers may deliver a given laser fluence at a lower cost than visible or ultraviolet lasers.

The fabrication of dye-sensitized solar cells currently employs a few micron-thick layer of nanocrystalline titania $TiO_2$ deposited on glass lamella. The very thin layers thus obtained offer a very large surface area that can be used to adsorb dyes. Example 3 illustrates the fabrication of devices with very thin layers of $TiO_2$ with adsorbed manganese meso-tetraphenylporphyrin sulfonate (MnTTPS), which behaves as a good photoacoustic reference under these conditions [37]. The same example also covers semiconductor materials that absorb strongly at the excitation wavelength, such as hematite, in the form of nanocrystalline, mesoporous α-Fe$_2$O$_3$ films, with fast electron-hole geminal recombination [38].

Thin films of materials with pulsed laser ablation thresholds below 50 mJ/cm$^2$ also meet the above-mentioned guidelines for fast and efficient conversion of the laser pulse energy into an acoustic transient. This is the case, for example, poly(ethylene terephthalate) (PET) [39], polyimide [40] and triazene polymers [28]. Additionally, these polymers have strong absorptions in the UV, with linear decadic absorption coefficients $\mu_a$=1.6×10$^5$ and 2.5×10$^5$ cm$^{-1}$ at 248 nm for PET and polyimide, respectively [27], and $\mu_a$≈10$^5$ cm$^{-1}$ at 308 nm for triazene polymers [28, 41]. With such high absorption coefficients, it is possible to have films with thicknesses of 200 nm that absorb more than 99% of the incident laser pulse of appropriate wavelength and undergo ablation with the production of high amplitude acoustic transients at laser fluences below 100 mJ/cm$^2$.

FIG. 1 compares acoustic transients produced by different devices under the same laser fluence and detected by a Panametrics 2.25 MHz transducer (model A106S) and digital storage oscilloscope (Tektronix DSA 601,1 Gs/s, two channels). The excitation employed the third harmonic of a Spectra-Physics Quanta Ray GCR 130 Nd:YAG laser (5-6 ns pulse width) with and energy per pulse ca. 10 mJ/cm$^2$ at 355 nm. The relative amplitudes of such acoustic transients depend of the sensitivity of the transducer to the various acoustic frequencies present in the acoustic transient wave. Thus, the amplitude of the acoustic transients measured by the transducer is only indicative of photoacoustic conversion efficiency attained by the devices. Nevertheless, the amplitudes of the acoustic transients produced by the devices designed in accordance with the guidelines given above are higher than that of the pressure wave generated by a 1 mm thick black polystyrene target.

Example 4 shows the influence of the linear absorption coefficient on the bandwidth of the acoustic transient wave. Using a Panametrics 225 MHz transducer (model V2113), it is shown that the fast Fourrier transform of acoustic transients generated by films with higher linear absorption coefficients have ultrasonic frequencies that extend to 200 MHz, FIG. 4. These high frequencies show that the acoustic transient follows the duration of the laser pulse (ca. 6 ns).

D. Biological Evaluation

The evaluation of the performance of photoacoustic waves generated by these devices in promoting the transdermal delivery of large molecules and biological materials is best done with animal models having skin structures that close resemble human skin. The best animal model to test skin permeation is the minipig, in view of the similarities between minipig and human skin characteristics and of their similar permeability to different drugs [42]. The proof of principle of the efficacy of the devices disclosed here is presented in Examples 5 through 8 with two clinically relevant entities: a porphyrin and a protein. Porphyrins and porphyrin derivatives are currently employed as photosensitizers in the photodynamic therapy of cancer. Their use in the treatment of skin cancers and of skin disorders such as actinic keratoses, squamous cell carcinoma, Bowen's disease (intra-epithelial squamous cell carcinoma) or basal cell carcinoma, is limited by the slow diffusion of these large molecules through the skin. The transdermal delivery of 5,10,15,20-tetrakis(2,6-fluoro-3-N-methylsulfamoylphenyl) porphyrin (F$_2$TPPMet, molecular weight 1131 Da) in minipig skin with devices disclosed here is described in Examples 5 and 7. Proteins are currently delivered by hypodermic needles for the treatment of various illnesses and disorders. A very relevant example is the subcutaneous injection of insulin (molecular weight 6 kDa) for the treatment of diabetes. Examples 6 and 8 describe the efficient intradermal administration of Green Fluorescent Protein (GFP, molecular weight 27 kDa) using devices disclosed here.

In vivo and in vitro tests employed four minipigs obtained from IMIDHA (Instituto Madrileño de Investigación y Desarrollo Rural, Agrario y Alimentario)—Aranjuez (Madrid). They were all females, aged 6-8 months, white with brown spots, average weight 56.8 kg (66.2, 57.1, 43.5, 60.6 kg). They were received at Estação Zootécnica Nacional, Vale de Santarém, where they were accommodated in individual boxes with 1.5 m$^2$, feed with a standard diet for pigs and water ad libidum, for an acclimation period of three weeks. The study was performed in accordance to the Portuguese ethical guidelines on a license granted by Direcção de Serviços de Saúde o Protecção Animal, ref. 0420/000/000/2007. Access to food was suspended 24 h hours before treatment. The backs of the animals were shaved 24 h prior to the in vivo application of the dermatological formulations. The formulations were the same for passive transdermal delivery and for active transdermal delivery with photoacoustic waves. The photoacoustic conversion devices and the laser employed in these experiments were described above. All procedures were carried out under anesthesia. The pre-medication employed 30 min in advance was: Azaperone (Stresril®—Veterinaria ESTEVE—Spain), 2 mg/kg intramuscular injection+atropine sulphate, 50 mg SC. The induction was done with ketamine (Clorketam®—Vétoquinol, France), 20 mg/kg, intramuscular injection. The anesthesia was maintained with endrotracheal intubation, using spontaneous ventilation with 2-3 l/min of oxygen+3% isoflurane (Isoflo®—Veterinária ESTEVE, Spain). The samples were collected from 3 minipigs under the anesthesia described above. Skin aliquots with sizes 20×20×10 (length, side, depth) were obtained by surgical excision. After the collection of the skin samples, the animals were then killed with an overdose of sodium thiopental (25 mg/kg)÷20 ml of 7.5% potassium chloride. The fourth minipig was followed by 3 weeks while feed with a standard diet for pigs and water ad libidum.

Skin sections were cut from the back of the minipigs after they had been sacrificed. These skin sections were frozen and kept at −18° C. until use in in vitro tests. Before each in vitro test, the required amount of minipig skin was slowly brought to room temperature. All the tests were carried out at room temperature.

The skin samples collected after the experiments were analyzed by microscopy to evaluate the penetration depth of the desired compounds, or followed an extraction procedure to evaluate their amounts under the skin. The evaluation of the penetration depth by fluorescence microscopy or by confocal microscopy requires tissue fixation. The first step in the fixation was immersion in paraformaldehyde (4% in aqueous solution) for at least 24 h. Next, the samples were transferred to a 25% sucrose solution for at least 48 h. Following this treatment, the skin samples become denser than the sucrose solution. An aliquot was extracted with a biopsy punch, frozen in dry ice and then mounted in holder with Tissue-Tek O.C.T. compound (Sakura Finetek Europe B.V., Zoeterwoude, The Netherlands) and cut in slices with controlled thicknesses selected between 25 and 100 mm in a cryostate. The skin slices were collected in microscope slides and kept refrigerated until they were analyzed by fluorescence microscopy and confocal microscopy. Alternatively, rather than using paraformaldehyde as a fixative, the skin samples were directly frozen in dry ice.

In order to evaluate the quantities of the $F_2$TPPMet delivered under the skin a specific method was developed. From the 1 cm² of experimental skin area, a 4 mm punch was taken and fully sectioned in the smallest pieces possible with a scalpel. Those pieces were transferred to a cup glass along with a certain volume of dichloromethane to be crushed with a shredder, YSTRAL Micro Shaft 6G. Afterwards, the remaining shredded skin undergoes an extraction procedure for 6 hours with a suitable solvent. For $F_2$TPPMet, dichloromethane represents the correct choice taking in account the lipophilicity of the skin and porphyrin. Fluorescence calibration curves of the pharmacological excipient delivered in the skin were performed in the extractor solvent to validate the methodology used. Finally, the mass delivered onto the skin is determined for each essay substituting its fluorescence in the calibration curve. The fluorescence signal of the fluorescence images was also quantified by analyzing the luminosity of $F_2$TPPMet delivered under the skin [43] after having outlined the areas where the fluorescence is observed. The extraction procedure for passive versus active transdermal delivery of $F_2$TPPMet confirmed the data obtained by fluorescence microscopy, namely the increase in the quantity of $F_2$TPPMet delivered to the skin when a high-impulse broadband pressure wave is employed as a method for active transdermal delivery.

Green Fluorescence Protein (GFP) has a molecular weight of 27 kDa that is much higher than proteins with therapeutic effects such as insulin (5.8 kDa). On the other hand, GFP has strong and characteristic light absorption and emission, which facilitate its analysis with fluorescence techniques, namely confocal microscopy. It was used here as a model for the intradermal delivery of proteins. Additionally, plasmids encoding GFP are commercially available, namely those based on gWIZ vectors. The expression level of GFP after transfection conducted by gWizGFP plasmids can be monitored by fluorescence, with excitation at 470-480 nm and emission at 510 nm. Example 9 presents in vitro proof-of-principle of plasmid transfection with gWizGFP.

DETAILED DESCRIPTION OF THE INVENTION

Example 1

Acoustic Transient Generation by Devices Incorporating Polymeric Films with Micrometer Thicknesses Manganese meso-tetraundecylporphyrin (MnTAP) is a good PAC reference compound and was incorporated in large amounts in a polystyrene film. The film was produced by spin-coating on a glass lamella. The glass functions as a window and the film is confined on the other side by a reflective plastic cover. This rigid device absorbs more than 90% of light at 355 nm, the absorbing material meets the criteria of a good PAC reference, the absorbing layer has a thickness ca. 30 µm, and the material in contact the skin has an acoustic impedance close to $Z_{skin}$. The acoustic impedance between all the layers can be improved with appropriate coupling media, such as acoustic scanning gel, paraffin or glycerin. The performance of this device under 355 nm laser pulse excitation by the third harmonic of a Nd:YAG laser with an energy density of 10 mJ/cm$^2$ measured by a 2.25 MHz transducer is compared in FIG. 1 against that of a 1 mm thick standard polystyrene plastic with a similar glass window.

This example illustrates the increase in photoacoustic conversion efficiency achieved by a device designed according to the guidelines disclosed in this invention, when compared with the efficiency of a simple black plastic target known in the art.

Example 2

Figure 1:
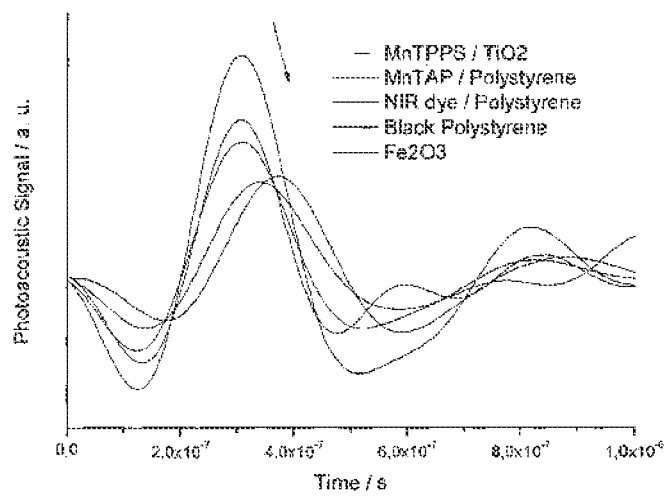
FIG. 1 compares photoacoustic waves produced by different devices under the sane laser fluence (10 mJ/cm²) and detected by a Panametrics 2.25 MHz transducer (model A106S) and digital storage oscilloscope (Tektronix DSA 601,1 Gs/s, two channels). The excitation employed the third harmonic of a Spectra-Physics Quanta Ray GCR 130 Nd:YAG laser (5-6 ns pulse width).
Figure 2:
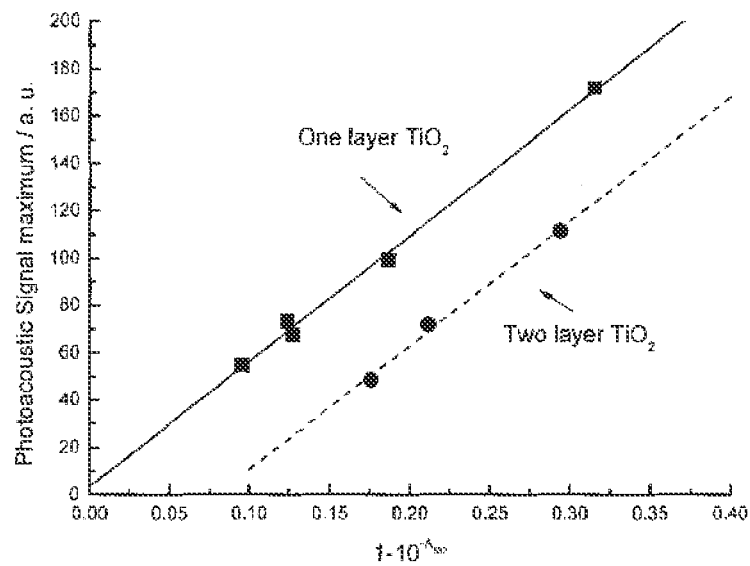
FIG. 2 shows that the amplitudes of the acoustic transients decrease when the thicknesses of the absorbing film are increased, in this case by adsorbing successive layers of $TiO_2$ nanoparticles on a glass slide. When a second layer is adsorbed, and the thickness is doubled, the amplitude of the acoustic transient generated by manganese tetraphenylporphyrin sulfonate (MnTTPS) adsorbed to the $TiO_2$ nanoparticles is reduced by half.
Figure 3:
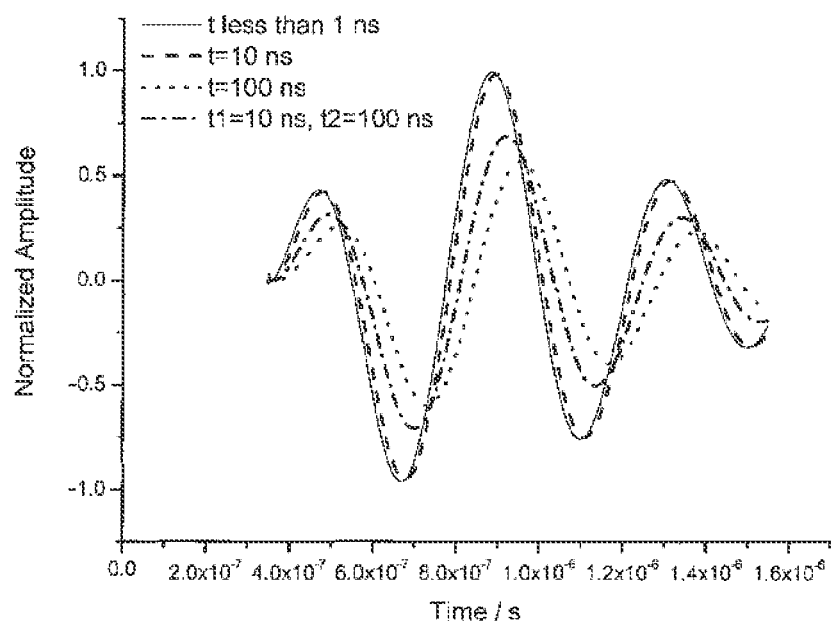
FIG. 3 illustrates simulations of photoacoustic waves as seen by a 2.25 MHz transducer, that are produced by the radiationless decay of one transient with a decay time of 10 ns or by the decay of one transient with a decay time of 100 ns, and the photoacoustic wave produced in the decay of two subsequent transients with lifetimes of 10 and 100 ns, each with 50% of the laser energy. The amplitude of photoacoustic waves decrease by a factor of 2 when the lifetime of the transient electronic state increases from 10 to 100 ns and its rise time is longer, thus reducing the impulse of the acoustic transient.

Acoustic Transient Generation by Devices Incorporating Infrared-Absorbing Dyes with Micrometer Thicknesses Infrared absorbing dyes employed in the fabrication of laser protective eyewear may also exhibit properties similar to those of PAC reference compounds. A film incorporating commercial EPOLIGHT 1178 dye powder from Epolin, with strong absorptions at 1064 and 355 nm, was prepared with the procedure described in Example 1. The photoacoustic waves produced by a film loaded with EPOLIGHT 1178 were compared with those produced by a similar film loaded with MnTAP, employing the same absorbances, laser fluences at 355 nm and other experimental conditions. The films produced very similar photoacoustic waves, demonstrating that EPOLIGHT 1178 has the properties of PAC reference compound. FIG. 1 compares the photoacoustic waves measured with the device incorporating EPOLIGHT 1178 with those measured with an analogous device but incorporating MnTAP, for the same laser fluence.

This example shows that a wide range of laser wavelengths may be employed in the efficiency conversion of laser pulses into photoacoustic waves, provided that the guidelines disclosed in this invention are followed.

Example 3

Acoustic Transient Generation by Devices Incorporating Nanostructured Layers of $TiO_2$ with Nano or Micrometer Thicknesses Methods to produce thin layers of nanostructured $TiO_2$ over a glass surface are very well known in the field of dye-sensitized solar cells. Contrary to such applications, the devices for transdermal drug delivery do not require the use of sintering to promote good electrical conductivity between the $TiO_2$ nanoparticles. On the contrary, sintering reduces the surface contact area.

Once meso-tetraphenylporphyrin sulfonate (MnTTPS) is adsorbed in sufficient amount to absorb more than 90% of the light at 355 nm, the lamella is dried and a thin layer of glycerol is added before a reflective metal sheet is placed on the top of it. This device is irradiated from the back, that is, the laser beam impinges on the glass lamella, traverses it and is absorbed by the dye absorbed in the $TiO_2$ nanocrystallites. Any light that is not absorbed by the dye is either absorbed or reflected by the metal surface, which blocks all light from going across the device. A layer of $TiO_2$ particles with larger sizes, for example 100-200 nm, may also be incorporated to increase light scattering and, consequently, increase optical path and the probability of light absorption by the adsorbed dye. FIG. 1 compares the photoacoustic waves measured with this device and excitation at 355 nm with those measured with the devices described in the previous examples, for the same laser fluence.

Example 4

Figure 4:
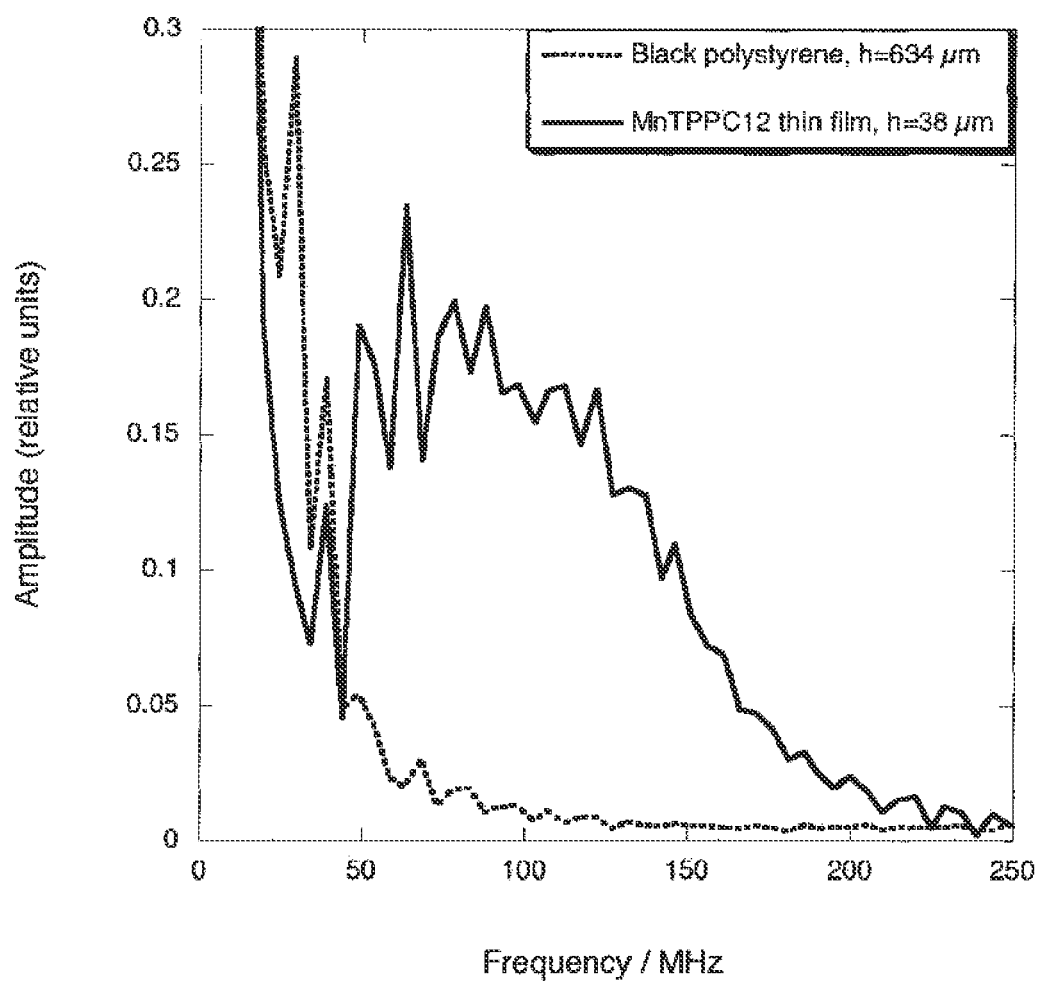
FIG. 4 shows the fast Fourier transform of photoacoustic waves measured by a 225 MHz Panametrics contact transducer following the pulsed laser excitation of either a 634 μm thick commercial black polystyrene disk or a 38 μm thick polystyrene film containing MnTAP, both of them absorbing more than 99.9% laser light at 484 nm. The excitation employed an EKSPLA OPO model PG-122 pumped by an EKSPLA NL301G Nd:YAG laser, delivering pulses with 4-6 ns pulse duration.
Figure 5:
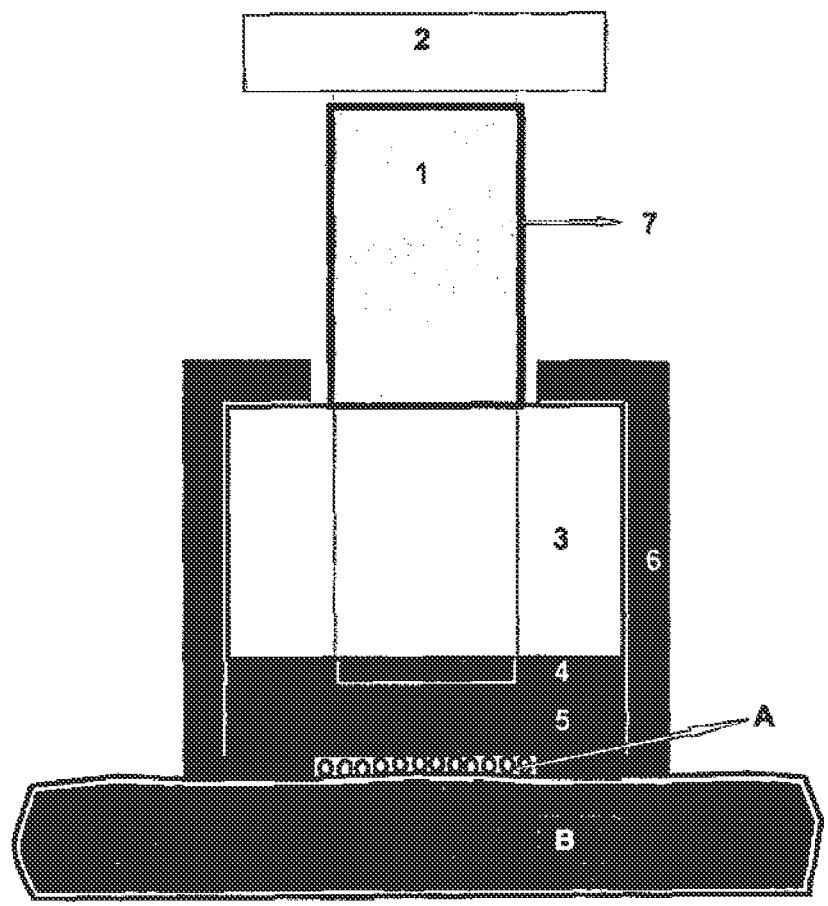
FIG. 5 is a schematic cross-section, not to the scale, of an embodiment of a device to deliver compounds in a suitable pharmacological formulation (A) through biological barriers (B) where the proximal end of an optical guide (7) is connected to a pulsed laser source and the distal end is directed to a thin absorbing layer (4) of a film containing a PAC reference compound. The optical guide provides directionality with or without physical contact between the laser source and the absorbing layer containing the PAC reference compound. One laser pulse (1) may be guided and/or focused to a part of the film (4) and subsequent laser pulses may be guided to the same or to different parts of the film (4). A rigid window element (3) is transparent to the wavelength of the laser pulse (1) that is selectively absorbed by the PAC reference compound incorporated in the thin film (4). The light transmitted through the film (4) is optionally reflected by a front-face mirrored support element (5) and makes a second passage, with more absorption, through the film (4). The photoacoustic wave produced in the film (4) is optionally transmitted through the support element (5) to the biological barrier (B), such as for example skin, with the acoustic coupling favored by the dermatologic formulation (A) containing the drug to be delivered to the skin (B). Close contact between window element (3), thin film (4) and support element (5) is provided by a structural element (6). This structural element may incorporate a technology to orient the laser pulse (1) and distribute subsequent laser pulses to different parts of the film (4).

Acoustic Transient Generation by Devices with High Linear Absorption Coefficients MnTAP can be incorporated in large quantities in thin polystyrene films. A 38 µm thick film was made with an absorptance of 1.8 at 647 nm, which corresponds to an absorptance larger 5 at 484 nm. Thus, this thin film has $\mu_a \gg 1300$ cm$^{-1}$ and the spectral band of a photoacoustic transient it may produce should be determined by the spectral band of the laser pulse absorbed by the thin film. The film was confined between a quartz window and the surface of a 225 MHz Panametrics transducer and excited by EKSPLA OPO model PG-122 pumped by an EKSPLA NL30G Nd:YAG laser, delivering pulses with 4-6 ns pulse duration at 484 nm. Fast Fourier transform of the photoacoustic transient detected lead to the spectral distribution presented in FIG. 4. Significant frequency components up to 200 MHz are present in the signal. The same figure also presents the fast Fourier transform of a signal obtained with a commercial black polystyrene disk with and absorptance larger 5 at 484 nm and measured in the same conditions. The signal generated by this device does not contain meaningful frequency components above 50 MHz.

Example 5

In Vitro Transdermal Delivery of a Porphyrin with Molecular Weight Ca 1 kDa

A dermatological formulation with $F_2$TPPMet was obtained dissolving 5 mg of this porphyrin in 0.556 ml absolute ethanol, next adding 1.737 ml of propylene glycol, followed by 0.22 ml of Azone and 0.3 ml of water. The mixture was thoroughly mixed in vortex and sonicated to facilitate the solubilization, and then added to the gel base, composed of water (76.65%), 96% ethanol (15%) glycerin (6%), triethariolamine (1.35%), carbopol 940 (1%). The mixture is thoroughly mixed to achieve a good homogenization. In this formulation, the final concentration of the prophyrin is 0.1% and that of Azone® is 4%.

Figure 6:
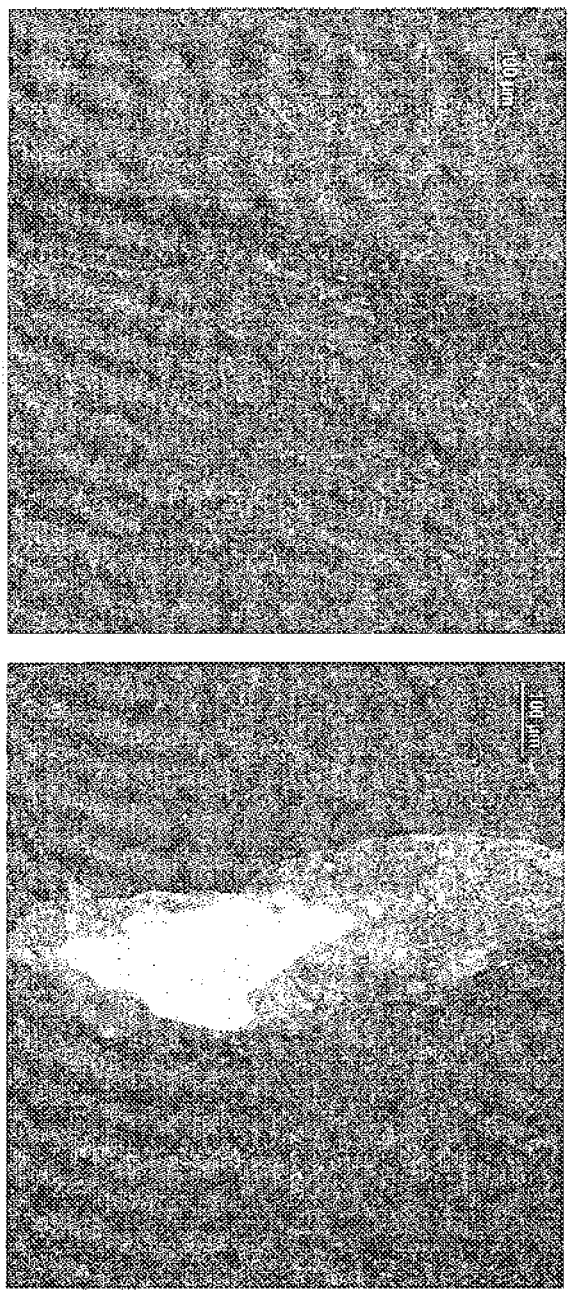
FIG. 6 compares the fluorescence microscopy of (A) passive and (B) active transdermal delivery of a porphyrin with molecular weight ca. 1 kDa through the skin of a minipig, with the device of Example 1 and 12 laser pulses at 355 nm with laser fluences of 10 mJ/cm², focused to an area of 1 cm², and an incubation time of 20 minutes.
Figure 7:
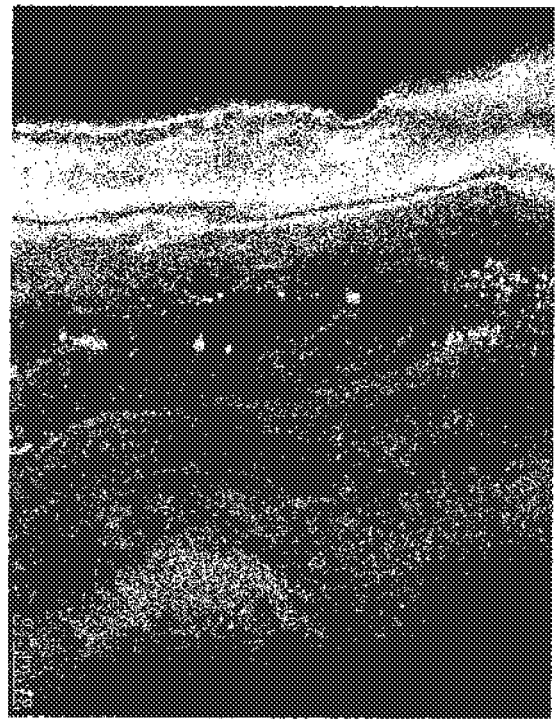
FIG. 7 shows the confocal microscopy of active transdermal delivery of a porphyrin with molecular weight ca. 1 kDa through the skin of a minipig, with the device of Example 3 and 6 laser pulses at 355 nm with laser fluences of 10 mJ/cm², and an incubation time of 20 minutes. Confocal mode: detector @1150 V, pin hole=111.44 μm and excitation @ 514 nm.

This formulation was applied to an approximately squared minipig skin sample, 2×2 cm, the device of Example 1 has gently pressured against the formulation and the skin, and 12 Laser pulses were fired with the second harmonic of a Nd:YAG laser (532 nm) with an energy per pulse of 50 mJ. The irradiated area was approximately 1 cm². The device was removed immediately following the irradiation, the treated area of the skin was covered with a 1 mm layer of the dermatological formulation and kept under occlusive dressing for 20 minutes. Once this time had elapsed, the formulation was removed with a spatula and washed with medical cotton embedded in ethanol, until no traces of the porphyrin could be seen in the medical cotton. The tissues were fixed with the procedure described above and analyzed by fluorescence microscopy, FIG. 6. FIG. 6 also shows the fluorescence microscopy obtained in an assay with only passive transdermal delivery the same dermatological formulation and the same time of contact of the formulation with the skin under occlusive dressing. FIG. 7 shows the results of a similar experiment but using the device of Example 3 and analysis of the skin sample with confocal microscopy.

Example 6

In Vitro Transdermal Delivery of a Protein with Molecular Weight Ca 27 kDa

A dermatological formulation containing Green Fluorescent Protein (GFP) was prepared as in the previous example, with GFP replacing $F_2$TPPMet.

Figure 8:
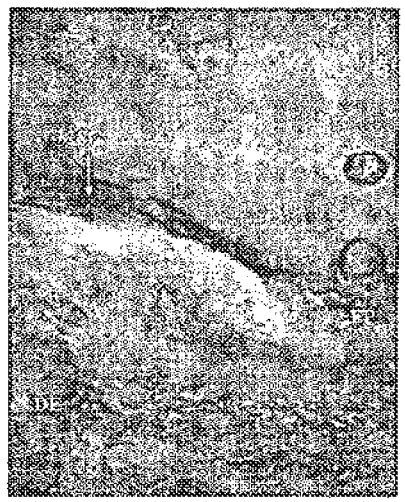
FIG. 8 shows the fluorescence microscopy (A) and the confocal microscopy (B) of active transdermal delivery of GFP (molecular weight 27 kDa) through the ex-vivo skin of a minipig with the device of Example 1 using 6 laser pulses at 355 nm with laser fluences of 50 mJ/cm², and an incubation time of 20 minutes. Confocal mode: detector @1150 V, pinhole=111.44 μm and excitation @ 488 nm.
Figure 8:
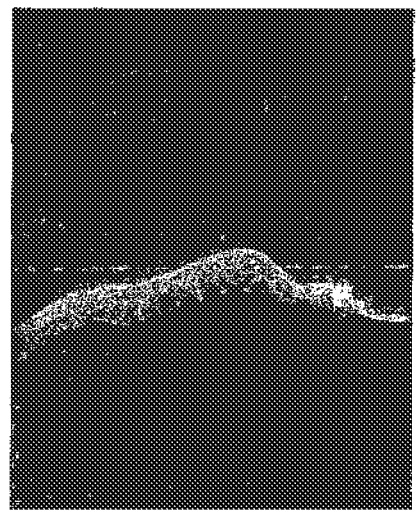

This formulation was applied to minipig skin samples with the device of Example 1 and the protocol of Example 5, namely promoting the transdermal delivery of GFP with 12 laser pulses of 50 mJ each and 20 minutes of contact of the formulation with the skin under occlusive dressing. The fluorescence microscopy and confocal microscopy of representative skin slices are presented in FIG. 8. Passive transdermal delivery of the same dermatological formulation and the same time of contact of the formulation with the skin occlusive dressing did not lead to a measurable amount of GFP in the skin.

Example 7

In Vivo Transdermal Delivery of a Porphyrin with Molecular Weight Ca 1 kDa

Passive and active in vivo transdermal tests were made on the back of minipigs. In each test the dermatological formulation containing a porphyrin was applied in a predetermined area of the skin for the desired amount of time, under occlusive dressing. Once that time had elapsed, the formulation was removed with a spatula and washed with medical cotton embedded in ethanol, until no traces of the formulation could be seen in the medical cotton. The skin samples were then surgically removed and the animals were sacrificed.

The dermatological formulation employed was that of Example 5. The handling of the animals was described above. While calm under the anesthesia, the formulations were applied by hand, using surgical gloves. Each application covered an approximately circular area 3 cm in diameter, with a thickness of a few millimeters of the gel. The application site allocated to passive drug delivery was covered with an occlusive patch. The application allocated to active drug delivery was covered with the device described in Example 1 and this was subject to 12 laser shots at 355 nm, with energies of 10 mJ per pulse and focused to an area ca 1 cm². The device was then removed, a thin layer of gel was added and the application site was covered with an occlusive patch. The patch was removed 20 minutes after the application, and the back of the animal was cleaned. The skin samples were collected as described before for three of the minipigs. Each sample was approximately rectangular, with 2 cm sides, and a thickness of 1 cm. The fourth minipig was kept alive for 10 days for subsequent evaluation. None of the animals, and in particular the animal that remained alive, showed evidence for side effects caused by the formulation with our without laser treatment.

Figure 9:
FIG. 9 shows the fluorescence microscopy of active transdermal delivery of a porphyrin with molecular weight ca. 1 kDa through the skin of a minipig in vivo, with the device of Example 1 using 12 laser pulses at 355 nm with laser fluences of 10 mJ/cm², and an incubation time of 20 minutes.

After fixative treatment, each sample was cut into slices for evaluations by fluorescence microscopy and by confocal microscopy. FIG. 9 shows representative examples of the images obtained by fluorescence microscopy. In 20 minutes, the porphyrin is distributed over all the epidermis while the stratum corneum remained intact.

Example 8

In Vivo Transdermal Delivery of a Protein with Molecular Weight Ca 27 kDa

Figure 10:
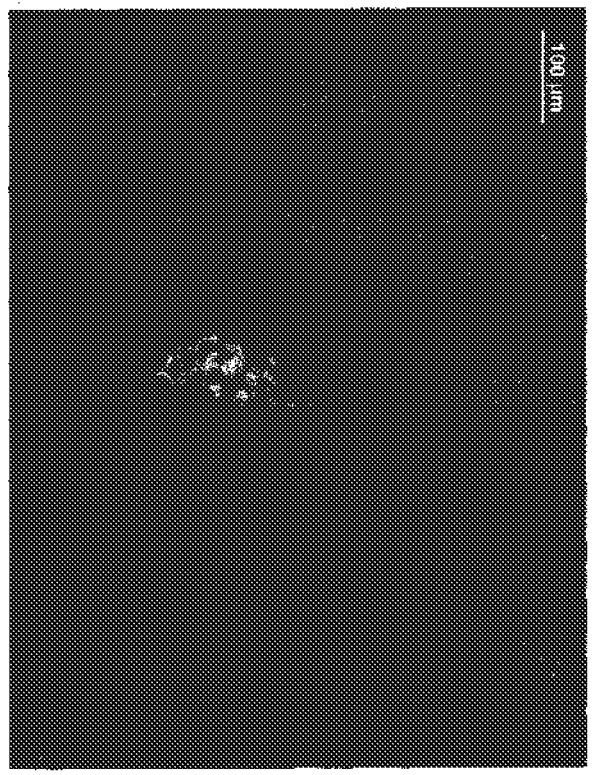
FIG. 10 shows the fluorescence microscopy of active transdermal delivery GFP through the skin of a minipig in vivo with the device of Example 1 using 12 laser pulses with laser fluences of 10 mJ/cm$^2$ at 355 nm, and an incubation time of 20 minutes.
Figure 11:
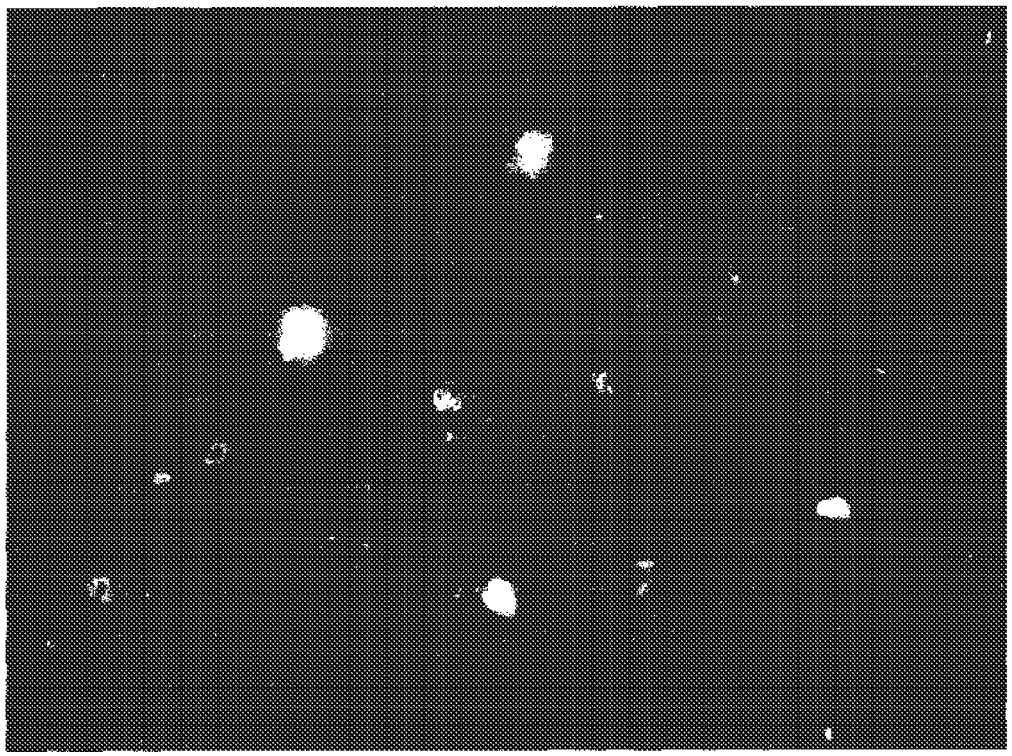
FIG. 11 shows the fluorescence microscopy of GFP produced after in vitro delivery of the gWizGFP plasmid into CCS-7 cells by using the device of Example 1 with laser pulses at 532 nm with laser fluences of 55 mJ/cm$^2$. Twenty-four hours after laser irradiation, the expression of GFP in the cells was observed by fluorescence microscope (DMIRE200 Leica). The cell samples were excited at 488 nm.

The dermatological formulation employed was that of Example 6. The device was described in Example 1. The protocol was that of Example 7. The incubation time after the application was kept at 20 minutes. After fixative treatment, the evaluation by fluorescence microscopy revealed the presence of GFP in a substantial part of the epidermis, while the stratum corneum remained intact, FIG. 10.

Example 9

In Vitro Gene Delivery

For proof of functional in vitro gene delivery into cells, COS-7 cells were cultured in Dulbecco's Modified Eagle Medium with 10% bovine serum and antibiotics (penicillin/streptomycin), in a cell culture incubator at 37° C. under an atmosphere of 5% $CO_2$ in air. After reaching 90% confluence, cells were harvested, seeded in culture dishes and incubated at 37° C. for 24 h. Before applying the pressure waves to the cells, an aqueous solution of the plasmid DNA coding GFP (gWizGFP, Aldevron, Fargo, N.J.) was added to the culture medium to attain a concentration of 100 µg/mL in the medium. The device of Example 1 was pressed against the bottom of the culture well, and laser pulses were fired with the second harmonic of a Nd:YAG laser (532 nm, 10

Hz, 31 mJ/pulse) for 3 minutes. The irradiated area was approximately 0.57 cm². Twenty-tour hours after laser irradiation, the expression of GFP in the cells was observed by use of fluorescence microscope (DMIRE200 Leica). Cells were also visualized using bright field. FIG. 12 presents the fluorescence microscopy of expressed GFP in COS-7 cells.

Other Embodiments

Persons skilled in the art recognize that there are many other ways to practice this invention using nanosecond and picosecond laser pulses and thin layers of very strongly absorbing materials with transient lifetimes similar or shorter than the laser pulse duration, other than the few examples described above. The compounds to be delivered to or through the skin can be applied in pharmacologically acceptable formulations before or after the action of the impulse transients generated at the thin absorbing layer by laser pulse absorption. The confinement and contact of the thin absorbing layer with the skin can be mediated by a variety of materials with similar impedances, provided that they are sufficiently thick to provide rigidity and yet sufficiently thin to keep the acoustic wave planar. Laser pulses in the ultraviolet, visible and infrared can be employed for electronic, vibronic or vibrational excitation.

Thus, the above examples are not limitations on the scope of the invention but mere exemplifications. Accordingly, the reader should determine the scope of the invention by the appended claims and their legal equivalents, and not by the examples given.

The invention claimed is:

1. A device for the conversion of the energy in a laser pulse (1) emitted by a respective pulsed laser source (2) into a high-impulse and broadband acoustic transient, capable of enhancing the delivery of at least one compound in a suitable pharmacological formulation (A) to or through a target biological barrier (B), including skin or soft tissue, characterized in that said laser pulse (1) has an optical power density in the range between 0.1 and 40 MW/cm², and the device comprises:
   a thin layer (4) of a conversion material including at least one molecular system, wherein said molecular system absorbs said laser pulse (1) and generates a high-impulse and broadband acoustic transient in said conversion material, by means of thermoelastic expansion and/or structural volume expansion and/or a photodecomposition;
   a structural and/or binding element (6) arranged so that it keeps said thin layer (4) of a conversion material and also a window element (3) and a support element (5) in close contact, thereby ensuring an acoustic coupling between all these three parts and the rigidity of the ensemble; and
   said pulsed laser source (2) disposed so as to illuminate at least 1 mm² of said thin layer (4) of a conversion material with said laser pulse (1), wherein said laser pulse (1) has a wavelength that is absorbed by said thin layer (4) of a conversion material.

2. The device according to claim 1, wherein said thin layer (4) of a conversion material is a film of nanocrystalline mesoscopic oxide or chalcogenide particles with high internal surface areas, incorporating a layer of at least one photoacoustic reference compound adsorbed on the nanoparticles, and wherein said photoacoustic reference compound absorbs at least part of the laser pulse (1).

3. The device according to claim 1, wherein said thin layer (4) of a conversion material is a polymer film incorporating at least one photoacoustic reference compound, wherein said photoacoustic reference compound absorbs at least part of the laser pulse (1).

4. The device according to claim 1, wherein said thin layer (4) of a conversion material is a layer of a solution containing at least one molecular system that absorbs at least part of the laser pulse (1), and the solvent has high thermoelastic parameters, at least as expressed by a respective Grüneisen coefficient.

5. The device according to claim 1, wherein said thin layer (4) of a conversion material is a polymer film with an ablation threshold below a laser fluence of 50 mJ/cm² for nanosecond pulsed lasers.

6. The device according to claim 1, wherein the thickness of said thin layer (4) of a conversion material is between 0.01 and 400 µm, and the device further comprises a window element (3) disposed between said thin layer (4) of a conversion material and said pulsed laser source (2), and wherein said window element (3) is rigid and transparent to said laser pulse (1) and has an acoustic impedance that is large in respect to that of the thin layer (4) of a conversion material and confines the expansion or projection of said acoustic transient on its side of said thin layer (4) of a conversion material.

7. The device according to claim 1, wherein said thin layer (4) of a conversion material absorbs more than 99% of the incident laser pulse in the depth of the first 100 µm of said conversion material exposed to said laser pulse (1) in the infrared, that promote electronic and/or vibrational and/or rotational excitation in said thin layer (4) of the conversion material, and the device includes said window element (3).

8. The device according to claim 1, wherein said laser source (2) delivers laser pulses with pulse durations between 0.1 and 100 ns.

9. The device according to claim 1, wherein said pulsed laser source (2) delivers energy per pulse between 0.1 and 100 mJ/cm².

10. The device according to claim 1, wherein it further comprises a support element (5) disposed with respect to said window element (3) on the other side of said thin layer (4) of a conversion material between said thin layer (4) of a conversion material and a target biological barrier (B), and wherein said support element (5) protects said target biological barrier (B) from direct laser irradiation, and has a predefined acoustic impedance in the range and/or close to that of said target biological barrier (B) and is mirrored so as to reflect most of the laser pulse (1) that was not absorbed by said thin layer (4) back through said thin layer (4) and said window element (3) and thus provide a second passage of the laser pulse (1) through the device.

11. The device according to claim 1, wherein the thickness of said support element (5), optionally mirrored, is between 0.1 and 10 mm.

12. The device according to claim 1, wherein said structural and/or binding element (6) may be rigid or flexible construction, or a sealing or a cement.

13. The device according to claim 1, wherein it further comprises an optical guide (7) capable of substantially directing said laser pulse (1) from said pulsed laser source (2) to said thin layer (4) of a conversion material, and wherein said optical guide (7) is at least one fiber optic with the proximal end coupled to the pulsed laser source (2) and the distal end directed to said window element (3).

14. The device according to claim 1, wherein said optical guide (7) is movable or directed to movable optics, and directs, through external or remote control, including by means incorporated in the structural element (6), successive laser pulses (1) to smaller and different parts of the thin layer (4) that absorbs at least part of the laser pulse (1), such that a sequence of laser pulses is absorbed in said different parts but a substantial part of the thin layer (4) is eventually irradiated.

15. A method of delivering at least one compound in a pharmaceutically acceptable formulation (A) to or through a biological barrier (B), including skin or soft tissues, the method comprising the steps of:
   placing an acoustically coupling medium or a pharmaceutically acceptable formulation (A) including said compound in contact with a target area of said biological barrier (B);
   placing the device according to claim 1, its support element (5), in substantially direct contact with said target area of said biological barrier (B);
   applying at least one laser pulse (1) emitted from a pulsed laser source (2) with a wavelength absorbed by the thin layer (4) of said device according to claim 1;
   producing at least one high-impulse and broadband acoustic transient;
   delivering said acoustic transient to said target area of said biological barrier (B) through materials, such as said support element (5), with similar acoustic impedances and/or low acoustic attenuation;
   removing the device according to claim 1 from close contact with said target area of said biological barrier (B);
   adding a layer of pharmaceutically acceptable formulation (A) containing said compound to said target area of said biological barrier (B);
   optionally covering the layer of said pharmaceutical formulation (A) with an occlusive patch for the time needed for the delivery of the desired quantity of said compound to said target area of said biological barrier (B).

16. The method according to claim 15, wherein the pharmaceutically acceptable formulation (A) includes a pharmaceutically acceptable carrier for intradermal and transdermal delivery of the compound, and wherein the carrier includes a permeation enhancer that transiently permeabilizes the skin and facilitates the permeation of the compound through the various skin layers.

17. The method according to claim 15 or 16, wherein the pharmaceutically acceptable formulation (A) is contained by patch and the device according to claim 1 is applied on said patch.

18. The method according to claim 15, wherein at least one laser pulse (1), a number of laser pulses is employed to map all the surface of said thin layer (4) with at least one laser pulse.

19. A method of delivering at least one compound through biological membranes that normally act as barriers to molecular transport, the method comprising the steps of:
   placing a biologically-compatible formulation including said compound in contact with said biological membrane;
   placing the device according to claim 1, by means of said support element (5), in acoustic coupling with said biological membrane;
   applying at least one laser pulse (1) from said pulsed laser source (2) with a wavelength absorbed by the thin layer (4);
   producing at least one high-impulse and broadband acoustic transient;
   delivering said acoustic transient to the membrane through said acoustically coupling medium;
   removing the device according to claim 1 and, optionally, placing more of the biologically-compatible formulation in contact with the membrane.

20. The method according to claim 19, wherein it further comprises the steps of:
   inserting the device according to claim 1 at least in part into the human body, wherein said device is provided with a sufficiently long and biologically-compatible optical guide (7), and
   bringing said thin layer (4) of a conversion material into proximity of the drug delivery site, wherein said site is a portion of the human body.

\* \* \* \* \*